United States Patent [19]

Takeno et al.

[11] 4,369,057

[45] Jan. 18, 1983

[54] PLANT GROWTH INHIBITING COMPOSITION

[75] Inventors: Tsuneyuki Takeno; Tetsuji Iwasaki, both of Wakayama; Shiro Hojō, Sakaide; Eiichi Kimura, Takamatsu, all of Japan

[73] Assignees: Kao Soap Co., Ltd.; Japan Hydrazine Company, Inc., both of Tokyo, Japan

[21] Appl. No.: 207,472

[22] Filed: Nov. 17, 1980

[30] Foreign Application Priority Data

Apr. 14, 1980 [JP] Japan .................................. 55-48850

[51] Int. Cl.$^3$ ............................................. A01N 43/58
[52] U.S. Cl. .......................................... 71/92; 71/78; 71/DIG. 1
[58] Field of Search ...................... 71/92, 78, DIG. 1

[56] References Cited

U.S. PATENT DOCUMENTS 4,150,966 4/1979 Tsuchiya et al. ..................... 71/78
4,182,621 1/1980 Otaga et al. .......................... 71/78

*Primary Examiner*—Catherine L. Mills
*Attorney, Agent, or Firm*—Oblon, Fisher, Spivak, McClelland & Maier

[57] ABSTRACT

A plant growth regulating composition comprising the choline salt of 6-hydroxy-3(2H)-pyridazinone and, as adjuvants, a polyoxyethylene oleyl ether and a triethanolamine alkyl-sulfate. The composition according to this invention can be prepared at a lower production cost and is easy to apply. When applied, it exhibits low toxicity, and good penetration and transferability.

2 Claims, No Drawings

PLANT GROWTH INHIBITING COMPOSITION

BACKGROUND OF THE INVENTION

The present invention relates to a plant growth regulating composition, and particularly to a plant growth regulating composition which comprises the choline salt of 6-hydroxy-3(2H)-pyridazinone (hereinafter referred to as MH) and, as adjuvants, a polyoxyethylene oleyl ether and a triethanolamine alkylsulfate.

Heretofore, various salts of MH have widely been used as sucker (axillary bud) inhibitors for tobacco plants, sprouting inhibitors for onions or Irish potatoes in storage, or growth regulating agents for wild weeds. However, such conventional salts of MH do not have sufficient penetration and transferability, and accordingly do not provide adequate effectiveness.

Accordingly, it has long been desired to develop an MH composition which has low toxicity, provides easy handling, has good penetration and good transferability and provides adequate effectiveness under all natural conditions.

SUMMARY OF THE INVENTION

Under the circumstances, the present inventors have conducted an extensive research on it, and as a result, have found that a composition prepared by mixing the choline salt of MH with a polyoxyethylene oleyl ether and a triethanolamine alkyl sulfate as adjuvants, has low toxicity, lets MH be absorbed from the leaf surfaces of plant in a short period of time thereby improving its effectiveness, whereby the amount of use can be reduced and the rain resistance can be improved. This invention has been made on the basis of the above discovery.

In one aspect of this invention, there is provided a plant growth regulating composition which comprises the choline salt of 6-hydroxy-3(2H)-pyridazinone and as adjuvants, polyoxyethylene oleyl ether and triethanolamine alkylsulfate.

DETAILED DESCRIPTION OF THE PREFERRED EMBODIMENTS OF THE INVENTION

Choline of the choline salt of MH constituting the main effective component of the plant growth regulating composition of the present invention, is widely distributed in animal or plant bodies and has little toxicity and a strong affinity to plants thus providing a merit that the penetration and transferability is good. Furthermore, choline is industrially readily available and therefore economical.

The polyoxyethylene oleyl ether to be used as an adjuvant is preferably an addition product containing 2 to 35 moles of oxyethylene. As the triethanolamine alkyl sulfate, the one having an alkyl group of 8 to 18 carbon atoms is preferred, and particularly preferred is triethanolamine laurylsulfate. The ratio of the polyoxyethylene oleyl ether to the triethanolamine alkylsulfate is preferably within a range of 1:1 to 1:0.5 (by weight). The ratio of the choline salt of MH to the adjuvants is preferably within a range of 1.36:1 to 5.2:1 (by weight).

According to the present invention, unexpectedly high effectiveness is obtainable by the combination of the choline salt of MH and the above-mentioned adjuvants. It is not possible to improve the effectiveness of the MH salt by using, instead of the polyoxyethylene oleyl ether, a well-known non-ionic surface active agent such as polyoxyethylene nonylphenyl ether, polyoxyethylene octylphenyl ether or polyoxyethylene fatty acid ester, or by using, instead of the triethanolamine alkylsulfate, a well-known anionic surface active agent such as an alkyl benzene sulfonate, an alkyl sulfosuccinate or an ammonium salt of laurylsulfuric acid.

The plant growth regulating composition of the present invention may be prepared by mixing or dissolving, for example, in water the choline salt of MH and the adjuvants in the above-mentioned ratios. It is possible to add a hydrophilic solvent, for instance, a $C_1$-$C_4$ lower alcohol such as methanol, ethanol or isopropanol, or $C_1$-$C_4$ alkylether of a glycol such as methyl cellosolve, ethyl cellosolve, butyl cellosolve, methyl carbitol, ethyl carbitol, or butyl carbitol; a turbidity inhibitor effective at a low temperature such as urea, glycerin, polyethylene glycol (molecular weight of up to 1000) or polypropylene glycol (molecular weight of up to 1000); or a defoaming agent such as methylsilicon, alkyl phosphate, or fatty acid.

It is preferred to prepare the composition of the present invention in a form of a concentrated solution containing, for instance, 30 to 55% by weight of the choline salt of MH and to dilute it for use with water, for example, 30 to 150 times (preferably 60 to 120 times) in the case of tobacco leaves or 60 to 200 times (preferably 60 to 150 times) in the case of eradication of weeds.

Now, the invention will be described with reference to the following examples.

EXAMPLE 1

To 88 parts by weight of an aqueous solution of the choline salt of MH (hereinafter referred to as C-MH aqueous solution), 12 parts by weight of the adjuvants were mixed to obtain a plant growth regulating composition. The C-MH aqueous solution contained 30.5% of MH, 58.8% of the choline salt of MH and the rest being water.

Said composition was diluted 300 times and applied to tobacco leaves (Virginia 115) cultured in the Wagner pot of 10 ares×1/50,000 after topping in early flower stage, at a rate of 5 ml per plant. The experiment was made with 4 series per section, and after expiration of 14 days, an average weight of suckers per plant was measured to determine the inhibition rate. The inhibition rate was calculated in accordance with the following formula. The results obtained are shown in Table 1. The numerals (p) in the brackets in the column for the adjuvants represent moles of the polyoxyethylene addition. Further, a comparison is made with compositions prepared by other than the present invention.

$$\text{Inhibition rate} = \frac{\begin{array}{c}\text{Average weight (g) of}\\\text{suckers per plant in}\\\text{the non-treated}\\\text{sections}\end{array} - \begin{array}{c}\text{Average weight (g)}\\\text{of suckers per}\\\text{plant in the}\\\text{treated sections}\end{array}}{\begin{array}{c}\text{Average weight (g) of}\\\text{suckers per plant}\\\text{in the non-treated}\\\text{sections}\end{array}}$$

TABLE 1

| | Composition | | | MH concentration at the time of application [%] | Average weight of suckers [g] | Inhibition rates [%] |
|---|---|---|---|---|---|---|
| | Aqueous MH solution (parts by weight) | Adjuvants (parts by weight) | Adjuvants (kinds and mixing proportions) [wt %] | | | |
| Products of the present invention | 88 | 12 | Polyoxyethylene ($\bar{p}$ = 8) oleyl ether/triethanolamine laurylsulfate/ methyl cellosolve/water = 21:21:16:42 | 0.089 | 1.35 | 83.5 |
| | 88 | 12 | Polyoxyethylene ($\bar{p}$ = 20) oleyl ether/triethanolamine laurylsulfate/ methyl cellosolve/water = 30:23:12:35 | 0.089 | 1.13 | 86.2 |
| Comparative products | 100 | 0 | Not added | 0.1 | 2.1 | 74.2 |
| | 100 (A-MH) | 0 | Not added | 0.1 | 2.7 | 66.9 |
| | 100 (K-HM) | 0 | Not added | 0.1 | 3.4 | 58.3 |
| Control | No Treatment | | | — | 8.16 | — |

(Note)
In the above Table, A-MH represents the diethanolamine salt of MH (an aqueous solution containing 30.5% of MH), K-MH represents the potassium salt of MH (an aqueous solution containing 30.5% of MH) and an aqueous MH solution without notes represents an aqueous C-MH solution.

It is apparent from Table 1 that the compositions of the present invention exhibit superior efficacy of sucker control to C-MH, A-MH, or K-MH, using no adjuvants, and that C-MH has a superior penetrability than A-MH or K-MH.

EXAMPLE 2

The following compositions were prepared in a manner similar to Example 1 and sucker inhibition experiments were carried out with respect to tobacco leaves.
The results obtained are shown in Table 2.

EXAMPLE 3

The following compositions were prepared in a manner similar to Example 1, and sucker inhibition experiments were carried out with respect to tobacco leaves. The results obtained are shown in Table 3.

TABLE 2

| | Composition | | | MH concentration at the time of application [%] | Average weight of suckers [g] | Sucker inhibition rates [%] |
|---|---|---|---|---|---|---|
| | Aqueous C-MH solution (parts by weight) | Adjuvants (parts by weight) | Adjuvants (compositions and mixing proportions) [wt %] | | | |
| Products of the present invention | 80 | 20 | Polyoxyethylene ($\bar{p}$ = 9) oleyl ether/triethanolamine laurylsulfate/methanol/water = 15:24:25:36 | 0.08 | 1.7 | 80 |
| | 80 | 20 | Polyoxyethylene ($\bar{p}$ = 20) oleyl ether/triethanolamine laurylsulfate/methanol/water = 30:20:20:30 | 0.08 | 1.7 | 80 |
| | 80 | 20 | Polyoxyethylene ($\bar{p}$ = 30) oleyl ether/triethanolamine laurylsulfate/methanol/water = 30:20:20:30 | 0.08 | 1.3 | 83 |
| Comparative products | 80 | 0 | Not added | 0.08 | 2.7 | 65 |
| | 100 | 0 | Not added | 0.1 | 2.3 | 70.0 |
| Control | No treatment | | | — | 7.7 | — |

TABLE 3

| | Composition | | | MH concentration at the time of application [%] | Average weight of suckers [g] | Sucker inhibition rates [%] |
|---|---|---|---|---|---|---|
| | Aqueous MH solution (parts by weight) | Adjuvant (parts by weight) | Adjuvants (compositions and mixing proportions) [wt %] | | | |
| Products of the present invention | 70 | 30 | Polyoxyethylene ($\bar{p}$ = 9) oleyl ether/triethanolamine laurylsulfate/methanol/water = 23:21:24:32 | 0.07 | 1.42 | 79.0 |
| | 70 | 30 | Polyoxyethylene ($\bar{p}$ = 20) oleyl | 0.07 | 1.11 | 83.6 |

TABLE 3-continued

| | Composition Aqueous MH solution (parts by weight) | Adjuvant (parts by weight) | Adjuvants (compositions and mixing proportions) [wt %] | MH concentration at the time of application [%] | Average weight of suckers [g] | Sucker inhibition rates [%] |
|---|---|---|---|---|---|---|
| | 70 | 30 | ether/triethanolamine laurylsulfate/methanol/water = 33:18:21:28 | 0.07 | 1.45 | 78.5 |
| | | | Polyoxyethylene ($\bar{p}$ = 30) oleyl ether/triethanolamine laurylsulfate/methanol/water = 33:18:21:28 | | | |
| Comparative products | 70 (K-MH) | 30 | Polyoxyethylene ($\bar{p}$ = 20) oleyl ether/polyoxyethylene ($\bar{p}$ = 20) nonyl phenyl sodium sulfate/ methanol/water = 33:18:21:28 | 0.07 | 3.20 | 55.3 |
| | 70 (K-MH) | 30 | Polyoxyethylene ($\bar{p}$ = 20) oleyl ether/triethanolamine laurylsulfate/methanol/water = 33:18:21:28 | 0.07 | 2.98 | 54.8 |
| | 70 | 30 | Polyoxyethylene ($\bar{p}$ = 20) oleyl ether/polyoxyethylene ($\bar{p}$ = 20) nonyl phenyl sodium sulfate/ methanol/water = 33:18:21:28 | 0.07 | 2.18 | 70.1 |
| | 70 | 0 | Not added | 0.07 | 2.59 | 61.7 |
| | 100 | 0 | Not added | 0.1 | 2.11 | 68.8 |
| Control | | | No treatment | — | 6.75 | — |

(Note)
In the above Table, K-MH represents the potassium salt of MH (an aqueous solution containing 30.5% of MH) and an aqueous MH solution without notes represents C-MH aqueous solution.

EXAMPLE 4

In a manner similar to Example 1, a homogeneous liquid composition was obtained by adding 33 parts of the adjuvants of the present invention to 67 parts of C-MH aqueous solution. This composition was diluted 60 times and applied to tobacco leaves (Virginia species: Va-115) cultivated in an agricultural field after topping in early flower stage at a rate of 20 ml per plant. The experiment was carried out with 4 series per section, and after expiration of 20 days the evaluation was made. A few compositions other than those of the present invention were tested for the purpose of comparison. The results obtained are shown in Table 4.

TABLE 4

| | Compositions Aqueous MH solution (parts by weight) | Adjuvants (parts by weight) | Adjuvants (kinds and mixing proportions) [wt %] | MH concentration at the time of application [%] | Suckers inhibition rates [%] | Toxicity |
|---|---|---|---|---|---|---|
| Product of the present invention | 67 | 33 | Polyoxyethylene ($\bar{p}$ = 8) oleyl ether/triethanolamine laurylsulfate/methanol/water = 23:22:23:32 | 0.34 | 98.4 | None |
| | 67 | 33 | Polyoxyethylene ($\bar{p}$ = 20) oleyl ether/triethanolamine laurylsulfate/methanol/water = 33:18:21:28 | 0.34 | 98.7 | None |
| Comparative product 1 | 67 | 33 | Polyoxyethylene ($\bar{p}$ = 8) oleyl ether/methanol/water = 34:21:45 | 0.34 | 85.3 | None |
| Comparative product 2 | 67 | 33 | Triethanolamine laurylsulfate/methanol/water = 23:21:56 | 0.34 | 83.5 | None |
| Comparative product 3 (sold on the market) | 99 (A-MH) | 1 | Polyoxyethylene alkylphenol ether/polyoxyethylene dodecyl ether/sodium laurylsulfate = 20:60:20 | 0.5 | 98.0 | None |

(Note)
In the above Table, A-MH represents the diethanolamine salt of MH (an aqueous solution containing 30.5% of MH) and an aqueous MH solution without notes means an aqueous C-MH solution.

It is apparent from Table 4 that the compositions of the present invention have superior efficacy of sucker control to the conventional A-MH product sold on the market although the effective concentration of MH was lower in the compositions of this invention, and that an synergistic effect is obtainable by the combination of polyoxyethylene oleyl ether and triethanolamine laurylsulfate.

EXAMPLE 5

A homogeneous liquid composition was obtained by mixing 70 parts of an aqueous C-MH solution and 30 parts of the adjuvants of the present invention in a manner similar to Example 1. The composition was diluted 60 times and applied to Dandelion Blowballs cultured for 50 days, after their sprouting in the Wagner pot of 10 ares×1/50,000, at a rate of 2 ml per plant and the MH absorption rates in the Dandelion Blowballs were measured after 2, 6, 24 and 30 hours.

The absorption rates were calculated by the following formula.

$$\text{Absorption rate (\%)} = \frac{\text{MH amount (mg) absorbed in leaves, stems and roots}}{\text{MH amounts (mg) absorbed in leaves, stems and roots} + \text{MH amounts (mg) attached to leaves and stems}} \times 100$$

The MH amounts attached to leaves and stems were obtained by washing the test samples with an aqueous solution containing 1% of sodium hydroxide and subjecting it to a quantitative analysis.

The results obtained are shown in Table 5.

TABLE 5

| Compositions | | | | | | | | MH concentration at the time of application (%) |
|---|---|---|---|---|---|---|---|---|
| Aqueous MH solution (parts by weight) | Adjuvants (parts by weight) | Adjuvant (kinds and mixing proportions) [wt %] | MH absorption rates (%) time (hr) | | | | | |
| | | | 0.5 | 2 | 6 | 24 | 30 | |
| Products of the present invention | 70 | 30 | Polyoxyethylene (p̄ = 8) oleyl ether/triethanolamine laurylsulfate/methanol/water = 23:22:23:32 | 15 | 46 | 79 | 91.2 | 92 | 0.35 |
| Comparative products | 100 | 0 | Not added | 5.2 | 21 | 35 | 63 | 70.2 | 0.5 |
| | | Standard A-MH | | 10.1 | 30.3 | 47 | 69.7 | 79.3 | 0.5 |

(Note)
In the above Table, Standard A-MH represents the same product as Comparative product 3 in Table 4 and, without any specific indication, an aqueous C-MH solution is meant.

It is apparent from Table 5 that the compositions of the present invention give very high absorption rates.

EXAMPLE 6

A homogeneous liquid composition was obtained by mixing 83 parts of C-MH and 17 parts of the adjuvants of the present invention in a manner similar to Example 1. The composition was diluted 60 times and applied to Horse Weed cultured to a height of 36 cm in an agricultural field, at a rate of 72 liters per 10 ares at the stems and leaves, and portions above the earth were cut off after 2, 4, 8, 24 and 96 hours after the treatment. Upon expiration of 30 days, the heights of newly-grown weed were measured to determine the inhibition rate. The inhibition rate was calculated by the following formula.

$$\text{Inhibition rate (\%)} = \frac{\begin{array}{l}\text{Average height (cm) of the non-}\\\text{treated weed newly grown during}\\\text{the 30 days after the cut-off}\\ - \text{Height (cm) of the treated weed}\\\text{newly grown during the 30 days}\\\text{after the cut-off}\end{array}}{\begin{array}{l}\text{Average height (cm) of the non-}\\\text{treated weed newly grown during}\\\text{the 30 days after the cut-off}\end{array}} \times 100$$

TABLE 6

| Compositions | | | | Inhibition rates (%) | | | | |
|---|---|---|---|---|---|---|---|---|
| Aqueous MH solution (parts by weight) | Adjuvants (parts by weight) | Adjuvants (kinds and mixing proportions) [wt %] | MH amounts per 10 ares (g) | Time for cutting off the portions above the earth after the application (hr) | | | | |
| | | | | 2 | 4 | 8 | 24 | 96 |
| Product of the present invention | 83 | 17 | Polyoxyethylene (p̄ = 20) oleyl ether/triethanolamine laurylsulfate/methanol/water = 22:23:20:35 | 300 | 75 | 81.3 | 87.5 | 89.3 | 98.3 |
| Comparative products | | | Standard A-MH | 360 | 43 | 65.2 | 69.7 | 78.3 | 90.6 |
| | | | Inhibition rate upon expiration of 30 days after application of the above product of the present invention without cutting off the portions above the earth. | 300 | | | 26% | | |

(Note) In the above Table, Standard A-MH represents the same product as Comparative product 3 in Table 4.

It is apparent from Table 6 that the composition of the present invention has good penetration and transferability into plants. Further, it is seen that a higher inhibition effectiveness is obtainable when the portions above the earth are cut off after the application of the composition and after the absorption of MH.

EXAMPLE 7

The composition of the present invention prepared in a manner similar to Example 4, was applied to onions and Irish potatoes cultured on earth in a green house, and the amounts of MH residue in the bulbs and tuberous roots were measured. The composition of the present invention was diluted 100 times with water, and applied at a rate of 80 liters per 10 ares. Upon expiration of 3 weeks after the application, the tubers and tuberous roots were dug out and the MH contents were measured.

The results are shown in Table 7.

A-MH was diluted 40 times and applied at a rate of 80 liters per 10 ares.

The results obtained are shown in Table 8.

TABLE 7

| | Compositions | | | | MH contents (ppm) | |
|---|---|---|---|---|---|---|
| | Aqueous MH solution (parts by weight) | Adjuvants (parts by weight) | Adjuvants (kinds and mixing proportions) [wt %] | MH amount per 10 ares and concentration (%) | Irish potatoes | Onions |
| Product of the present invention | 67 | 33 | Polyoxyethylene ($\bar{p}$ = 8) oleyl ether/triethanolamine laurylsulfate/methanol/ water = 23:22:23:32 | 160 g 0.2% | 21.3 | 10.3 |
| Comparative product | | | Standard A-MH | 240 g 0.3% | 18.7 | 8.9 |

(Note)
In the above table, Standard A-MH represents the same product as Comparative product 3 in Table 4.

TABLE 8

| | Compositions | | | | | | |
|---|---|---|---|---|---|---|---|
| | Aqueous MH solution (parts by weight) | Adjuvants (parts by weight) | Adjuvants (kinds and mixing proportions) [wt %] | Covering rate of the regenerated Kudzu-vine* | Number of regenerated Kudzu-vines per m² | Length of new vines | Amounts (g) and concentrations (%) of MH per 10 ares |
| Product of the present invention | 88 | 12 | Polyoxyethylene ($\bar{p}$ = 20) oleyl ether/ triethanolamine laurylsulfate/methyl cellosolve/water = 30:23:12:35 | 1 | 0.3 | 9.5 | 422 (g) 0.52 (%) |
| Comparative product | | | Standard A-MH | 1.5 | 0.5 | 10.3 | 600 (g) 0.75 (%) |
| Control | | | No application area | 100 | 14.3 | 213 | — |

*Proportion (%) of the earth surface covered by the leaves of Kudzu-vines.
(Note)
In the above table, Standard A-MH represents the same product as Comparative product 3 in Table 4.

It is apparent from Table 7 that in spite of the fact that the amount of application of the composition of the present invention was less than that of A-MH, the composition of the present invention was absorbed in a greater amount thus indicating superior penetration and transferability.

EXAMPLE 8

1.6 kg of the composition of the present invention prepared by Example 1 was diluted 50 times by water and applied to leaves of Kudzu-vine grown at road sides at a rate of 80 liters per 10 ares (October 15) and the regeneration state was investigated next spring (May 12). For the purpose of comparison, 2 kg of Standard A-MH was diluted 40 times and applied at a rate of 80 liters per 10 ares.

What is claimed is:

1. A plant growth inhibiting composition comprising the choline salt of 6-hydroxy-3(2H)-pyridazinone and, as adjuvants, a polyoxyethylene oleyl ether, which is an addition product of oleyl alcohol with 2 to 35 mols of ethylene oxide, and a triethanolamine alkylsulfate having an alkyl group of 8 to 18 carbon atoms, wherein the weight ratio of said polyoxyethylene oleyl ether and triethanolamine alkylsulfate is from 1:1 to 1:0.5, and the weight ratio of said choline salt of 6-hydroxy-3(2H)-pyridazinone to said polyoxyethylene oleyl ether and triethanolamine alkylsulfate is from 1.36:1 to 5.2:1.

2. The plant growth inhibiting composition as claimed in claim 1, wherein said triethanolamine alkylsulfate is triethanolamine laurylsulfate.

* * * * *